US008607795B2

(12) United States Patent
Cuevas et al.

(10) Patent No.: US 8,607,795 B2
(45) Date of Patent: Dec. 17, 2013

(54) BALLOON CUFF TRACHEOSTOMY TUBE (75) Inventors: Brian J. Cuevas, Cumming, GA (US);
Michael Sleva, Atlanta, GA (US); James F. Schumacher, Cumming, GA (US);
Michael A. Kenowski, Alpharetta, GA (US); Sam C. Chan, Alpharetta, GA (US); Ryan C. Frank, Westerville, OH (US)

(73) Assignee: Kimberly-Clark WorldWide, Inc., Neenah, WI (US)

( * ) Notice: Subject to any disclaimer, the term of this patent is extended or adjusted under 35 U.S.C. 154(b) by 1019 days.

(21) Appl. No.: 12/206,517

(22) Filed: Sep. 8, 2008

(65) Prior Publication Data

US 2009/0090366 A1 Apr. 9, 2009

Related U.S. Application Data (60) Provisional application No. 60/994,664, filed on Sep. 20, 2007.

(51) Int. Cl.
*A62B 9/06* (2006.01)
*A61M 16/00* (2006.01)

(52) U.S. Cl.
USPC .............................. 128/207.14; 128/200.26

(58) Field of Classification Search
USPC .............. 128/207.14–207.16, 203.12, 203.28
See application file for complete search history.

(56) References Cited

U.S. PATENT DOCUMENTS 2,693,182 A 11/1954 Phillips
3,481,339 A 12/1969 Millet Puig
(Continued)

FOREIGN PATENT DOCUMENTS

CA 2 296 308 A1 2/1999
CA 2 353 007 A1 6/2000
(Continued)

OTHER PUBLICATIONS

American Society for Testing Materials (ASTM) Designation: D 790-99, "Standard Test Methods for Flexural Properties of Unreinforced and Reinforced Plastics and Electrical Insulating Materials," pp. 150-158, published Feb. 2000.

(Continued)

*Primary Examiner* — Stephen Crow
(74) *Attorney, Agent, or Firm* — James B. Robinson (57) ABSTRACT

There is provided a balloon cuffed tracheostomy tube with a balloon designed so as to enhance the tube's anchorability without sealing the tracheal stoma. The tracheostomy tube device includes a conventional curved hollow tube. The distal end of the tube is adapted for insertion through a tracheal stoma and into the tracheal lumen of a patient's throat. The device further includes an inflatable balloon enveloping a portion of the tube. The balloon has a distal portion substantially centered about and attached to the distal end portion of the tube. The balloon also has a proximal portion attached to the bend region of the tube and positioned substantially off-center relative to the proximal portion of the tube and about the bend region below the proximal plane of the device. Upon inflation, this configuration provides for expansion of the balloon around the distal end portion of the tube and the proximal end portion of the tube below the proximal plane of the device to seal the trachea below the tracheal stoma and to avoid sealing the trachea above the tracheal stoma. This configuration of the balloon should allow secretions to exit the stoma so that they do not accumulate and become a possible source of ventilator acquired pneumonia.

3 Claims, 10 Drawing Sheets

(56) References Cited

U.S. PATENT DOCUMENTS

| | | | |
|---|---|---|---|
| 3,543,751 A | 12/1970 | Sheffer | |
| 3,659,612 A | 5/1972 | Shiley et al. | |
| 3,688,774 A | 9/1972 | Akiyama | |
| 3,693,624 A | 9/1972 | Shiley et al. | |
| 3,731,692 A | 5/1973 | Goodyear | |
| 3,889,688 A * | 6/1975 | Eamkaow | 128/207.15 |
| 3,901,246 A | 8/1975 | Wallace | |
| 3,973,569 A | 8/1976 | Sheridan et al. | |
| 3,987,798 A | 10/1976 | McGinnis | |
| 4,009,720 A | 3/1977 | Crandall | |
| 4,018,231 A | 4/1977 | Wallace | |
| 4,033,353 A | 7/1977 | La Rosa | |
| 4,091,816 A * | 5/1978 | Elam | 128/207.15 |
| 4,141,364 A | 2/1979 | Schultze | |
| 4,156,428 A | 5/1979 | Henkin | |
| 4,178,937 A | 12/1979 | Taylor et al. | |
| 4,246,897 A | 1/1981 | Muto | |
| 4,248,222 A | 2/1981 | Jaeger et al. | |
| 4,270,778 A | 6/1981 | Brownell | |
| 4,278,081 A | 7/1981 | Jones | |
| 4,280,492 A | 7/1981 | Latham | |
| 4,304,228 A | 12/1981 | Depel | |
| 4,305,392 A | 12/1981 | Chester | |
| 4,327,720 A * | 5/1982 | Bronson et al. | 128/207.15 |
| 4,327,721 A | 5/1982 | Goldin et al. | |
| 4,331,142 A | 5/1982 | Degen | |
| 4,340,046 A | 7/1982 | Cox | |
| 4,459,984 A | 7/1984 | Liegner | |
| 4,471,776 A | 9/1984 | Cox | |
| 4,596,248 A | 6/1986 | Lieberman | |
| 4,607,643 A * | 8/1986 | Bell et al. | 600/528 |
| 4,627,433 A | 12/1986 | Lieberman | |
| 4,649,913 A | 3/1987 | Watson | |
| 4,886,059 A | 12/1989 | Weber | |
| 4,979,505 A | 12/1990 | Cox | |
| 4,987,895 A | 1/1991 | Heimlich | |
| 5,056,515 A | 10/1991 | Abel | |
| 5,067,496 A | 11/1991 | Eisele | |
| 5,067,497 A | 11/1991 | Greear et al. | |
| 5,076,268 A * | 12/1991 | Weber | 128/207.15 |
| 5,188,592 A * | 2/1993 | Hakki | 604/35 |
| 5,285,777 A | 2/1994 | Beckwith | |
| 5,311,864 A | 5/1994 | Huerta | |
| 5,334,146 A | 8/1994 | Ozasa | |
| 5,339,808 A * | 8/1994 | Don Michael | 128/207.15 |
| 5,339,809 A | 8/1994 | Beck, Jr. et al. | |
| 5,392,774 A * | 2/1995 | Sato | 128/207.15 |
| 5,443,063 A * | 8/1995 | Greenberg | 128/207.15 |
| 5,443,064 A | 8/1995 | Theis et al. | |
| 5,458,139 A | 10/1995 | Pearl | |
| 5,501,215 A | 3/1996 | Huerta | |
| 5,653,230 A | 8/1997 | Ciaglia et al. | |
| 5,653,231 A | 8/1997 | Bell | |
| D398,989 S | 9/1998 | Ashlin | |
| 5,819,734 A | 10/1998 | Deily et al. | |
| 5,865,176 A * | 2/1999 | O'Neil | 128/207.15 |
| 6,036,697 A * | 3/2000 | DiCaprio | 606/108 |
| 6,053,167 A | 4/2000 | Waldeck | |
| 6,105,577 A | 8/2000 | Varner | |
| 6,135,111 A | 10/2000 | Mongeon | |
| 6,248,099 B1 | 6/2001 | Bell | |
| 6,284,179 B1 | 9/2001 | Deily et al. | |
| 6,286,509 B1 | 9/2001 | Nash et al. | |
| 6,460,540 B1 | 10/2002 | Klepper | |
| 6,526,977 B1 | 3/2003 | Göbel | |
| 6,544,224 B1 * | 4/2003 | Steese-Bradley | 604/103.06 |
| 6,550,475 B1 * | 4/2003 | Oldfield | 128/200.26 |
| 6,612,305 B2 | 9/2003 | Fauza | |
| 6,637,435 B2 | 10/2003 | Hague et al. | |
| 6,662,804 B2 | 12/2003 | Ortiz | |
| 6,725,862 B2 | 4/2004 | Klinberg et al. | |
| 6,745,773 B1 | 6/2004 | Gobel | |
| 6,814,077 B1 | 11/2004 | Eistert | |
| 6,840,242 B2 | 1/2005 | McCoy | |
| 6,971,382 B1 | 12/2005 | Corso | |
| 7,036,510 B2 | 5/2006 | Zgoda et al. | |
| 7,037,562 B2 | 5/2006 | Jimenez | |
| 7,040,321 B2 | 5/2006 | Göbel | |
| 7,086,402 B2 | 8/2006 | Peterson | |
| 7,141,046 B2 * | 11/2006 | Perkins et al. | 604/514 |
| 7,195,016 B2 | 3/2007 | Loyd et al. | |
| 7,258,120 B2 * | 8/2007 | Melker | 128/207.14 |
| 7,341,061 B2 * | 3/2008 | Wood | 128/207.29 |
| 8,177,769 B2 * | 5/2012 | Perkins et al. | 604/516 |
| 2001/0022415 A1 | 9/2001 | Laksin | |
| 2002/0014238 A1 | 2/2002 | Kotmel | |
| 2002/0165523 A1 * | 11/2002 | Chin et al. | 604/523 |
| 2003/0066532 A1 | 4/2003 | Gobel | |
| 2003/0139762 A1 | 7/2003 | Lee | |
| 2005/0065468 A1 | 3/2005 | Goebel | |
| 2005/0081861 A1 * | 4/2005 | Nasir | 128/207.14 |
| 2005/0166926 A1 | 8/2005 | Nomori | |
| 2006/0124134 A1 * | 6/2006 | Wood | 128/207.29 |
| 2006/0157061 A1 | 7/2006 | Loyd et al. | |
| 2006/0184109 A1 | 8/2006 | Gobel | |
| 2006/0201516 A1 * | 9/2006 | Petersen et al. | 128/207.14 |
| 2007/0095351 A1 | 5/2007 | Gobel | |
| 2007/0289596 A1 | 12/2007 | Campbell et al. | |
| 2007/0296125 A1 | 12/2007 | Colburn et al. | |
| 2008/0092902 A1 | 4/2008 | Schnell | |
| 2008/0142016 A1 | 6/2008 | Colburn et al. | |
| 2009/0025729 A1 | 1/2009 | Nomori | |
| 2009/0090365 A1 | 4/2009 | Cuevas et al. | |
| 2009/0091066 A1 | 4/2009 | Sleva et al. | |
| 2009/0209908 A1 | 8/2009 | Cuevas et al. | |

FOREIGN PATENT DOCUMENTS

| | | |
|---|---|---|
| CH | 408 292 A | 2/1964 |
| DE | 44 01 904 A1 | 7/1995 |
| EP | 0 003 322 B1 | 5/1981 |
| EP | 0 037 719 A1 | 10/1981 |
| EP | 0 052 483 A1 | 5/1982 |
| EP | 0 072 230 A1 | 2/1983 |
| EP | 0 078 685 A1 | 5/1983 |
| EP | 0 106 780 A1 | 4/1984 |
| EP | 0 107 779 A1 | 5/1984 |
| EP | 0 155 331 A1 | 9/1985 |
| EP | 0 371 752 A1 | 6/1990 |
| EP | 0 489 507 A1 | 6/1992 |
| EP | 0 586 717 A1 | 3/1994 |
| EP | 0 598 948 A1 | 6/1994 |
| EP | 0 747 077 A2 | 12/1996 |
| EP | 0 768 096 A2 | 4/1997 |
| EP | 1 004 328 A1 | 5/2000 |
| EP | 1 005 877 A2 | 6/2000 |
| EP | 1 044 701 A2 | 10/2000 |
| EP | 1 210 953 A1 | 6/2002 |
| EP | 1 219 317 A2 | 7/2002 |
| EP | 0 822 842 B1 | 8/2002 |
| EP | 0 930 909 B1 | 5/2003 |
| EP | 1 329 239 A1 | 7/2003 |
| EP | 1 003 584 B1 | 10/2003 |
| EP | 1 200 150 B1 | 3/2004 |
| EP | 1 803 478 A1 | 7/2007 |
| EP | 1 806 158 A1 | 7/2007 |
| GB | 0 019 196 A | 4/1907 |
| GB | 1 040 425 A | 8/1966 |
| GB | 1 113 484 A | 5/1968 |
| GB | 1 153 863 A | 5/1969 |
| GB | 2 056 285 A | 3/1981 |
| GB | 2 174 303 A | 11/1986 |
| GB | 2 324 735 A | 11/1998 |
| GB | 2 335 362 A | 9/1999 |
| GB | 2 429 919 A | 3/2007 |
| JP | 05-031192 A | 2/1993 |
| JP | 10-005340 A | 1/1998 |
| JP | 10-337326 A | 12/1998 |
| JP | 2003-093512 A | 4/2003 |
| JP | 2005-270319 A | 10/2005 |
| WO | WO 80/00307 A1 | 3/1980 |
| WO | WO 84/02657 A1 | 7/1984 |
| WO | WO 87/01293 A1 | 3/1987 |
| WO | WO 89/12425 A1 | 12/1989 |

(56) References Cited

FOREIGN PATENT DOCUMENTS

| | | |
|---|---|---|
| WO | WO 91/06342 A1 | 5/1991 |
| WO | WO 92/07602 A1 | 5/1992 |
| WO | WO 93/24170 A1 | 12/1993 |
| WO | WO 94/15657 A1 | 7/1994 |
| WO | WO 96/37250 A1 | 11/1996 |
| WO | WO 96/40339 A1 | 12/1996 |
| WO | WO 96/40340 A2 | 12/1996 |
| WO | WO 99/32169 A2 | 7/1999 |
| WO | WO 99/38548 A2 | 8/1999 |
| WO | WO 99/53989 A1 | 10/1999 |
| WO | WO 00/32262 A1 | 6/2000 |
| WO | WO 00/62849 A1 | 10/2000 |
| WO | WO 01/24861 A1 | 4/2001 |
| WO | WO 01/83015 A1 | 11/2001 |
| WO | WO 02/28462 A1 | 4/2002 |
| WO | WO 2004/016308 A2 | 2/2004 |
| WO | WO 2004/060439 A2 | 7/2004 |
| WO | WO 2004/069316 A2 | 8/2004 |
| WO | WO 2004/071553 A2 | 8/2004 |
| WO | WO 2004/096330 A2 | 11/2004 |
| WO | WO 2004/096331 A2 | 11/2004 |
| WO | WO 2004/101046 A1 | 11/2004 |
| WO | WO 2004/101048 A2 | 11/2004 |
| WO | WO 2005/016427 A2 | 2/2005 |
| WO | WO 2005/058401 A1 | 6/2005 |
| WO | WO 2006/029070 A2 | 3/2006 |
| WO | WO 2006/037626 A2 | 4/2006 |
| WO | WO 2006/087032 A1 | 8/2006 |
| WO | WO 2006/089961 A1 | 8/2006 |
| WO | WO 2006/099434 A1 | 9/2006 |
| WO | WO 2006/100426 A1 | 9/2006 |
| WO | WO 2006/125006 A2 | 11/2006 |
| WO | WO 2006/138138 A1 | 12/2006 |
| WO | WO 2007/000127 A1 | 1/2007 |
| WO | WO 2007/012060 A2 | 1/2007 |
| WO | WO 2007/016335 A1 | 2/2007 |
| WO | WO 2007/017447 A2 | 2/2007 |
| WO | WO 2007/024315 A1 | 3/2007 |
| WO | WO 2007/062162 A1 | 5/2007 |
| WO | WO 2007/069766 A1 | 6/2007 |
| WO | WO 2007/092199 A2 | 8/2007 |
| WO | WO 2007/149202 A1 | 12/2007 |
| WO | WO 2007/149203 A2 | 12/2007 |
| WO | WO 2007/149301 A2 | 12/2007 |
| WO | WO 2008/034751 A1 | 3/2008 |
| WO | WO 2008/034872 A1 | 3/2008 |
| WO | WO 2008/042130 A1 | 4/2008 |
| WO | WO 2008/042133 A2 | 4/2008 |
| WO | WO 2008/047978 A1 | 4/2008 |

OTHER PUBLICATIONS

American Society for Testing Materials (ASTM) Designation: D1238-04c, "Standard Test Method for Melt Flow Rates of Thermoplastics by Extrusion Plastometer," pp. 1-14, published Dec. 2004.
American Society for Testing Materials (ASTN) Designation: D2240-05, "Standard Test Method for Rubber Property—Durometer Hardness," pp. 1-13, published Sep. 2005.

* cited by examiner

BALLOON CUFF TRACHEOSTOMY TUBE

This application claims the benefit of commonly assigned U.S. provisional application 60/994,664, filed Sep. 20, 2007.

BACKGROUND OF THE INVENTION

As concerns about ventilator acquired pneumonia (VAP) continue to mount in the practice of medicine, particularly in the developed world, attention has been focused on ways to reduce the frequency and severity of this potentially fatal condition. It has been found that one source of bacterial leading to pneumonia can come from secretions from the throat of patients intubated with endotracheal tubes (ET tubes) for long periods of time. ET tubes are inserted into the mouth and down the throat past the glottis, and because of this cause a great deal of inflammation and generation of secretions from the tissues surrounding the tube. The discomfort that results from the location of the ET tube in the throat and the inflammation caused by the ET tube means that most patients are kept sedated while an ET tube is inserted.

In contrast to the practice of medicine using ET tubes, patients may be awake after the installation of a tracheostomy tube (trach tube). The trach tube, more importantly, is inserted through an opening or stoma in the front of the throat of the patient, bypassing the glottis and other internal obstacles above the throat. This is critically important since bypassing these organs does not inflame them nor does it provoke the release of secretions in large amounts.

As a result of the advance in understanding of the role of ET tubes in possibly promoting VAP and the prophylactic effect of trach tubes, medical practitioners are moving patients from ET tubes to trach tubes at earlier and earlier times during their hospitalization.

This heightened awareness of the role of intubation in the onset of VAP has caused increased scrutiny of the design of trach tubes as well, since although the amount of secretions is lower with trach tubes than with ET tubes, it is not nonexistent. Conventional tracheostomy tubes typically have a curved tube that serves as an artificial passage for the exchange of air between a patient and an air source, typically either atmospheric air or a mechanical respirator or ventilator. The distal end of the tube is usually equipped with a small, inflatable balloon, also called a cuff, which can be filled with a fluid (e.g., air). The balloon adheres to the internal lining of the trachea in its generally cross-sectional dimension in order to prevent air insufflated by the respirator into a patient from escaping to the environment through the tracheostomy or the larynx and pharynx. This enables the air to reach the lower airways and eventually the pulmonary alveoli. The balloon also aids in supporting the tube inside the trachea.

Figure 1:
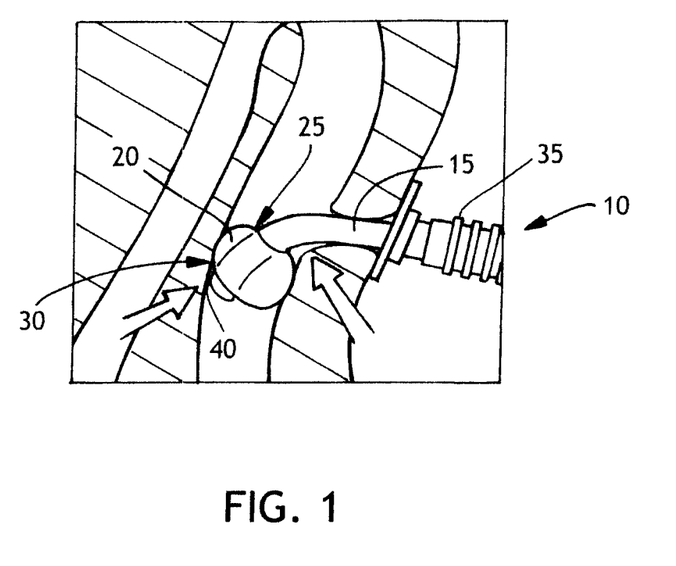
FIG. 1 is an illustration of a conventional cuffed tracheostomy tube within a trachea.

Conventional trach tubes, unfortunately, are generally not well anchored within the body, as shown in FIG. 1. As a result, the tube can move a great deal inside the airway, as well as through the tracheal stoma and the wound. This instability and lack of anchorage can lead to a number of problems. Another issue caused by the poor anchoring of trach tubes in the trachea is that they may be accidentally dislocated, sometimes coming out of the airway completely. The reintroduction of the tube can be very difficult, since the stoma may be inflamed or damaged by the removal of the original tube. Additionally, even under normal installation conditions, the distal tip of the trach tube can cause damage and inflammation to the posterior wall of the trachea if it rubs against the tracheal wall as the patient moves, coughs, etc.

Other suggestions for controlling the movement of trach tubes with balloons that expand to hold the tube have been proposed. An example of such a balloon is shown in U.S. Pat. No. 6,612,305 illustrated in FIG. 2. While these tracheostomy tube devices may provide suitable control over the movement of the tube, the balloons appear to seal the tracheal stoma, thus limiting access to that region. Sealing the tracheal stoma inhibits the removal of secretions through the stoma and can result in the same problems as ET tubes vis a vis VAP.

A trach tube design that is more stable within the trachea than currently available tubes is desirable. A trach tube that allows secretions to be removed through the stoma in order to avoid the accumulation of secretions above the balloon, potentially causing VAP, would be an improvement over both the ET tube and currently available trach tubes.

SUMMARY

The technology disclosed herein concerns a balloon cuffed tracheostomy tube with a balloon designed so as to enhance the tube's anchorability without sealing the tracheal stoma.

The tracheostomy device includes a conventional hollow tube having a proximal end portion, a distal end portion, and a bend region intermediate of the end portions. The distal end portion of the tube is arranged for insertion through a patient's throat and tracheal stoma and into the tracheal lumen such that the distal end portion of the tube extends in a first direction within the tracheal lumen when the proximal end portion extends in a second direction through the tracheal stoma. The proximal end portion defines a proximal plane of the device.

The device further includes an inflatable balloon enveloping a portion of the tube. More particularly, the balloon has a distal balloon portion substantially centered about and attached to the distal end portion of the tube. The balloon also has a proximal balloon portion attached to the bend region of the tube and positioned substantially off-center about the bend region below the proximal plane of the device. Upon inflation, this configuration provides for expansion of the balloon around the distal end portion of the tube and the proximal end portion of the tube below the proximal plane of the device to seal the trachea below the tracheal stoma and avoid sealing the trachea above the tracheal stoma. Desirably, this configuration of the balloon will allow secretions to exit the stoma.

The tracheostomy tube device may have balloon walls that are non-uniform in thickness. For example, the device may have a first portion of the balloon in which the walls have a thickness of about 20 to 30 micrometers and a second portion of the balloon in which the walls have a thickness of about 5 to about 15 micrometers. Desirably, the first portion of the balloon is the portion of the balloon contacting the upper portion of a cross-sectional region of the tracheal lumen and the second portion of the second balloon is the portion of the balloon contacting the lower portion of the same cross-sectional region of the tracheal lumen.

The inflatable balloon component may include a distal end, a distal attachment zone, a proximal end, a proximal attachment zone, an upper region and a lower region, wherein the upper region has a thickness of from about 15 to about 30 micrometers and the lower region has a thickness of from about 5 to about 15 micrometers.

The balloon component may be formed from thermoplastic polyurethane polymers, thermoplastic polyolefin elastomers, thermoplastic polyolefin block copolymers, SBS di-block elastomers, SEBS tri-block elastomers, polyvinyl chloride, polyethylene terephthalate and blends and mixtures thereof.

The trach tube device may further include a flexible conduit along the tube and the balloon such that secretions eventually accumulating cranially to the tracheal stoma can be removed. Suction may be applied to the conduit and secretions evacuated.

The device further includes means for inflating and deflating the balloon. These means for inflating and deflating the balloon may be conventional flexible conduits and fittings.

DETAILED DESCRIPTION

Conventional tracheostomy tubes are inserted through a stoma in the throat that has been dilated in order to receive the trach tube. Their "anchoring" or the controlled location of the tube within the trachea remains a concern with these known tubes. FIG. 1 is an illustration of such a conventional cuffed tracheostomy tube 10 composed of a tube 15 and an inflatable cuff 20. In this configuration, the cuff 20 is centered on the tube 15 at the proximal point of attachment 25 and the distal point of attachment 30 and these points of attachment located on the tube 15 are contiguous or at an angle of approximately 180 degrees.

In FIG. 1 illustration, the balloon is deformed as a result of compressive forces on the inflated balloon. These compressive forces may be caused by the weight of the ventilator tubing 35 or by movement of the patient that presses the ventilator tubing against an obstacle, or by other causes. These compressive forces may cause the distal tip 40 of the trach tube to impinge on the posterior surface of the trachea, indicated by the left arrow in FIG. 1, and may inflame or damage this surface.

Figure 2:
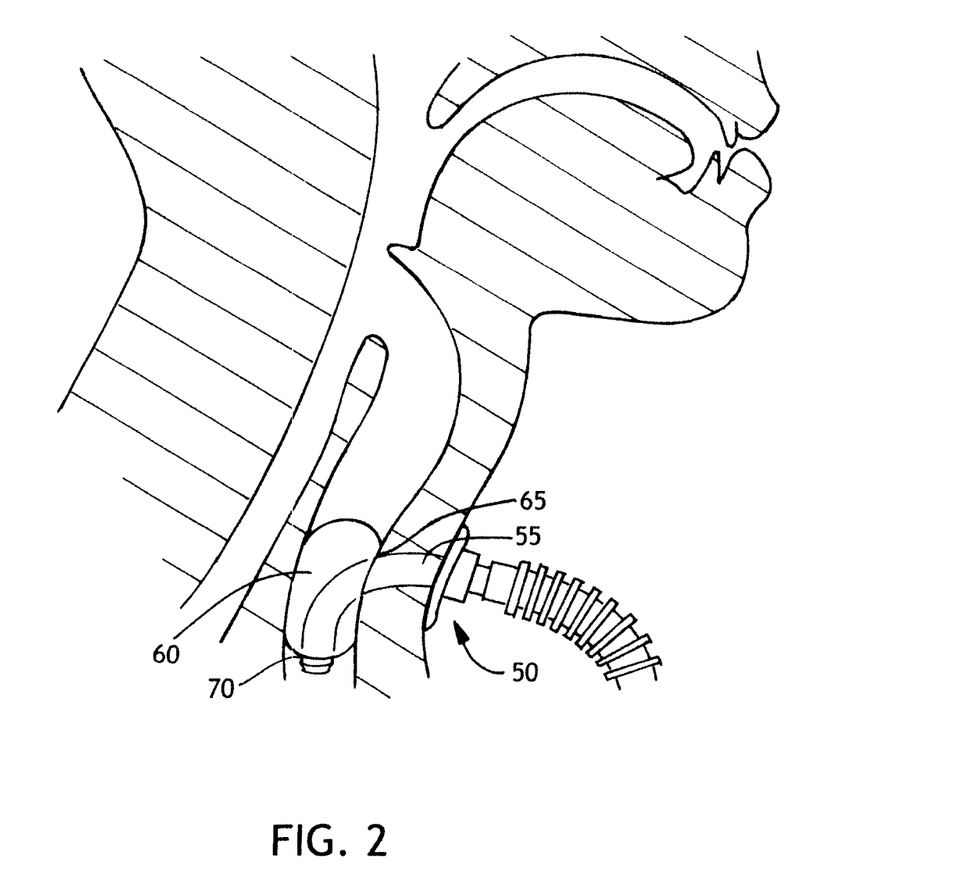
FIG. 2 is an illustration of a conventional elongated cuffed tracheostomy tube within a trachea

In contrast to the configuration of FIG. 1, FIG. 2 is an illustration of an elongated cuffed trach tube device 50 as generally described in U.S. Pat. No. 6,612,305. This trach tube has a tube 55 and an inflatable balloon cuff 60 surrounding the tube 55. In this configuration the cuff 60 expands not only around the tube 55, as do the current models, but also cranially to it and to the stoma. This occurs because the proximal point of attachment 65 and the distal point of attachment 70 of the inflatable cuff 60 on the tube 55 are not contiguous as they are in the device of FIG. 1. Stated another way, these points 65, 70 are at an angle (α) other than 180 degrees relative to conventional device shown in FIG. 1.

Figure 3:
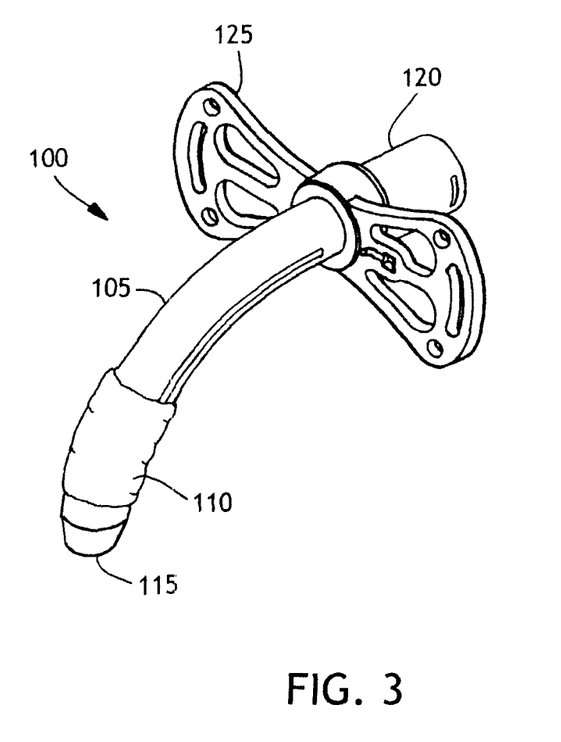
FIG. 3 is a drawing of a tracheostomy tube device prior to insertion into a trachea and prior to inflation of the balloon.

In order to enhance understanding of the general design of trach tubes, FIG. 3 is a view of a trach tube device 100 prior to insertion into the trachea and prior to inflation of the balloon 110. The tube 105 has a distal end 115 and a proximal end 120. The proximal end 120 may be connected to a ventilator (not shown) if mechanical ventilation of the patient is needed. The tube has a flange 125 that lies against the skin of the throat after the device is in place. The flange may be sutured to the skin and/or connected to a strap encircling the head of the patient to help to hold the device in place.

Figure 4:
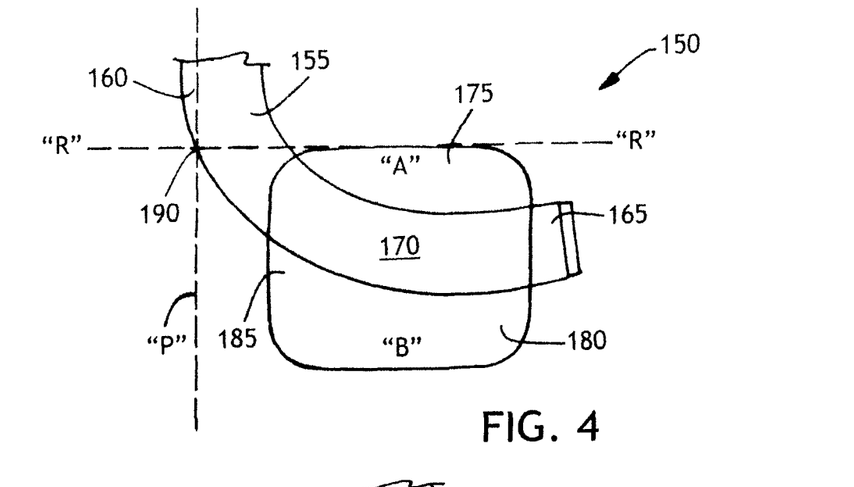
FIG. 4 is an illustration of an exemplary balloon cuffed tracheostomy tube designed so as to enhance the tube's anchorability without completely sealing the tracheal stoma.
Figure 5:
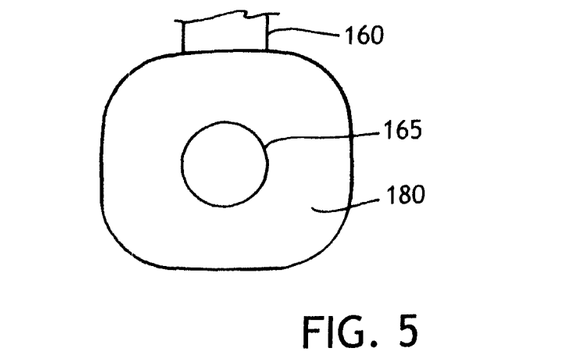
FIG. 5 is a frontal view of an exemplary tracheostomy tube device.
Figure 6:
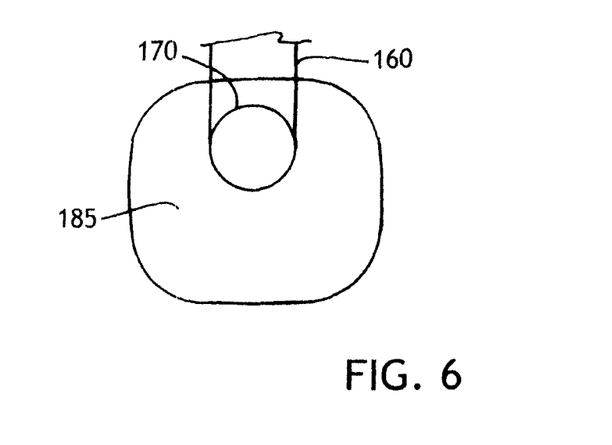
FIG. 6 is a rear view of an exemplary tracheostomy tube device.

Returning to the device as described in the Summary, FIGS. 4, 5 and 6 show various views of the balloon cuffed tracheostomy tube 150 distal to the flange, with the balloon designed so as to enhance the control of the location of the tube without completely sealing the tracheal stoma. This tracheostomy tube device 150 includes a conventional hollow tube 155 having a proximal end portion 160, a distal end portion 165, and a bend region 170 intermediate of the end portions. The distal end portion of the tube is arranged for insertion through a patient's throat and tracheal stoma and into the tracheal lumen such that the distal end portion of the tube extends in a first direction within the tracheal lumen when the proximal end portion extends in a second direction through the tracheal stoma.

FIG. 4 illustrates that the proximal end portion 160 defines a proximal plane of the device "P". Generally speaking, the proximal plane of the device is a plane that runs along the portion of the tube as it passes the stoma just inside the tracheal lumen that is closest to the patient's head, i.e. the edge of the stoma in the cranial direction. The disclosed device further includes an inflatable balloon 175 enveloping a portion of the tube 170. As illustrated, the balloon 175 has a distal balloon portion 180 substantially centered about and attached to the distal end portion of the tube 155. The balloon also has a proximal balloon portion 185 attached to the bend region of the tube and positioned substantially off-center about the bend region 170 below the proximal plane of the device "P". "Substantially off-center" as used herein means that the center of the tube is at least one tube radius away from the center of the balloon as it exits the balloon, more desirably at least one tube diameter away from the center of the balloon.

After insertion of the devise illustrated in FIG. 4, the balloon is inflated. Upon inflation, this configuration provides for expansion of the balloon 175 around the distal end portion of the tube 165 and the proximal end portion of the tube 160 below the proximal plane of the device "P" to seal the trachea below the tracheal stoma and avoid sealing the trachea above the tracheal stoma. Secretions should have easy access to the stoma where they may be removed by absorption into a stoma pad placed below the flange attached to conventional trach tubes at the throat. More particularly, a stoma pad or other secretion media may be placed between the skin of the throat and the trach tube flange. This pad may be removed and disposed of on a regular basis and replaced with a fresh pad so that bacteria does not accumulate above the stoma.

With further reference to FIG. 4 it should be noted that while various curvatures of the bend region of conventional hollow tracheal tubes may result in the proximal plane being located slightly more or slightly less forward, the proximal plane of the device "P" may be readily determined from a reference line "R" running parallel to the upper surface of the inflatable balloon 175 (while inflated). The proximal plane of the device "P" is the plane that is perpendicular to the reference line "R" and which passes through the point 190 where the reference line "R" intersects with the most proximal or outermost portion of the tube 155. This is generally thought to correspond to a plane that runs along the portion of the tube as it passes the stoma just inside the tracheal lumen that is closest to the patient's head, i.e. the edge of the stoma in the cranial direction.

FIG. 5 is a frontal view of the tracheostomy tube device 150 of FIG. 4, illustrating the distal portion of the tube 165 and the distal balloon portion 180. Note that the distal portion of the tube 165 exits the balloon 180 in approximately the center of the balloon 180. This tube location is not substantially off-center from the center of the balloon.

FIG. 6 is a rear view of the tracheostomy tube device 150 illustrating the proximal portion of the tube 160 and the bend region 170 of the tube and the proximal balloon portion 185. Note that the proximal portion of the tube 160 exits the balloon 180 in a location that is substantially off-center of the balloon 180. For, example, the center of the tube in FIG. 6 is about one tube diameter (approximately about 8 to 10 mm) away from the center of the balloon as the tube exits the balloon. That is, the center of the tube is vertically displaced about one tube diameter away from the center of the balloon in only one axis (that is, in the vertical axis of the tracheostomy tube) as depicted in FIG. 6. As used herein, the term "substantially off-center" refers to the relative position of the proximal portion of a tracheostomy tube at its point of attachment to a tracheostomy tube balloon, particularly in comparison to distal portion of a tracheostomy tube at its point of attachment to the same tracheostomy tube balloon. As noted above, the amount of displacement is desirably about one tube diameter (approximately 8 to 10 mm) but distances greater than one tube diameter such as, for example, 15 mm or 20 mm or more, are contemplated.

The measurement of balloon wall thicknesses may be made using a Litematic device. An exemplary device is the series 318 Model VL-50A by Mitutoyo America Corporation. According to the manufacturer, the Litematic device measures thicknesses between 0 and 50.8 mm with a resolution of 0.01 micron, using a probe tip and an inflexible ceramic base. The measuring force used is 0.01N (1 gram). The probe tip used for testing herein was a 3 mm diameter carbide ball contact point which was provided as the "standard" probe tip with the Litematic device.

Strips of single-ply foils or membranes may be used to determine the thickness of each sample. Balloon specimens (not attached to a trach tube) from each sample may be cut to prepare the strips: first the ends should be cut off to leave a uniform band of about 30 mm in width; then each band should be cut in the width direction to form a strip. Thickness measurements at 10 locations along the length of each strip should be made, the individual measurements of strips for each sample (with at least 6 strips measured) should be averaged together, and the respective standard deviations calculated.

Figure 7:
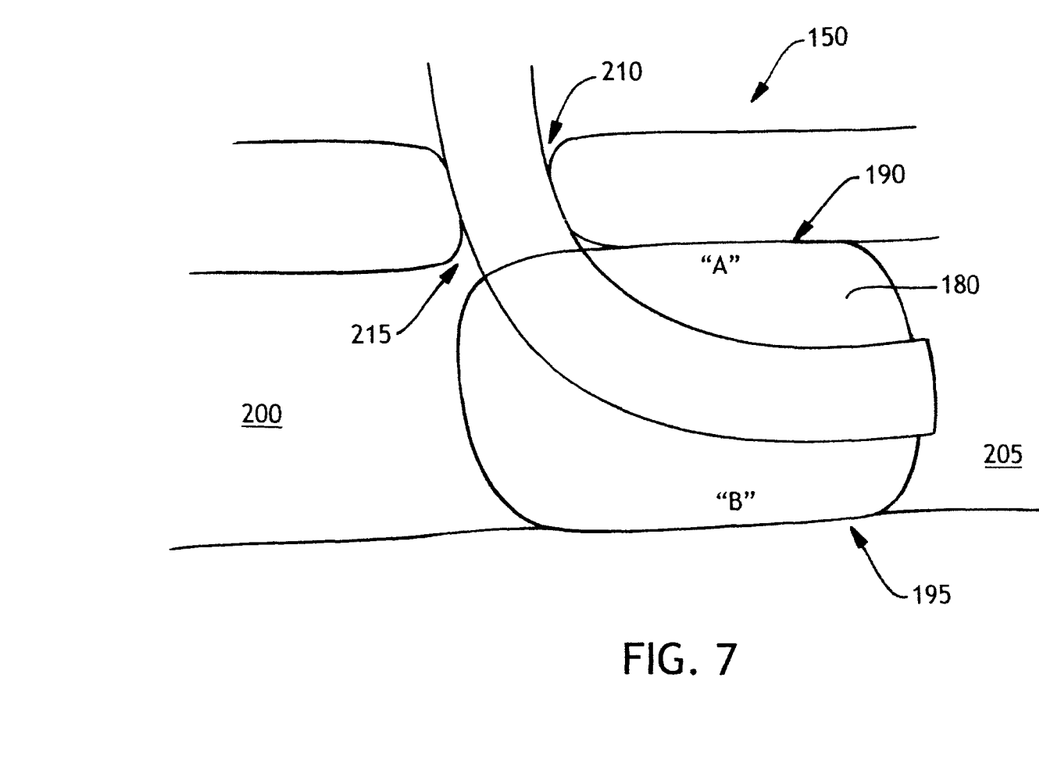
FIG. 7 is an illustration of an exemplary device in which the balloon is inflated to seal the trachea in the region below the tracheal stoma while avoiding sealing the trachea in the region above the tracheal stoma.

FIG. 7 is a cross sectional view of the tracheostomy tube device in a trachea. As discussed briefly above, the balloon 180 may have walls that are non-uniform in thickness. The device may, for example, have a first portion "A" of the balloon in which the walls have a thickness of about 20 to 30 microns and a second portion "B" of the balloon in which the walls have a thickness of about 5 to about 15 micron. It is believed desirable that the first portion "A" of the balloon 180 is the portion of the balloon contacting the upper (anterior) portion of a cross-sectional region of the tracheal lumen 190 and the second portion "B" of the balloon is the portion of the balloon contacting the lower (posterior) portion of the same cross-sectional region of the tracheal lumen. Stated somewhat differently, the inflated balloon 180 is adapted to seal the trachea (i.e., the tracheal lumen 200) in the region 205 below the tracheal stoma 210 and to avoid completely sealing the trachea in the region of the tracheal stoma. This configuration of the balloon allows secretions to exit the stoma at the opening 215.

Although the inventors should not be held to a particular theory of operation, it is generally thought that having the relatively thinner second portion "B" of the balloon contacting the posterior wall 195 of the trachea will provide a better seal in that region where secretions may be more prone to collect due to gravity when a patient is resting horizontally on his back. The relatively thicker first portion "A" of the balloon contacts the upper wall 190 of the trachea where secretions may be less prone to collect when a patient is resting horizontally on his back. Once the patient stands or sits up, gravity no longer holds the secretions against the posterior wall of the trachea and they may exit the trachea through the stoma in the anterior tracheal wall.

Figure 8:
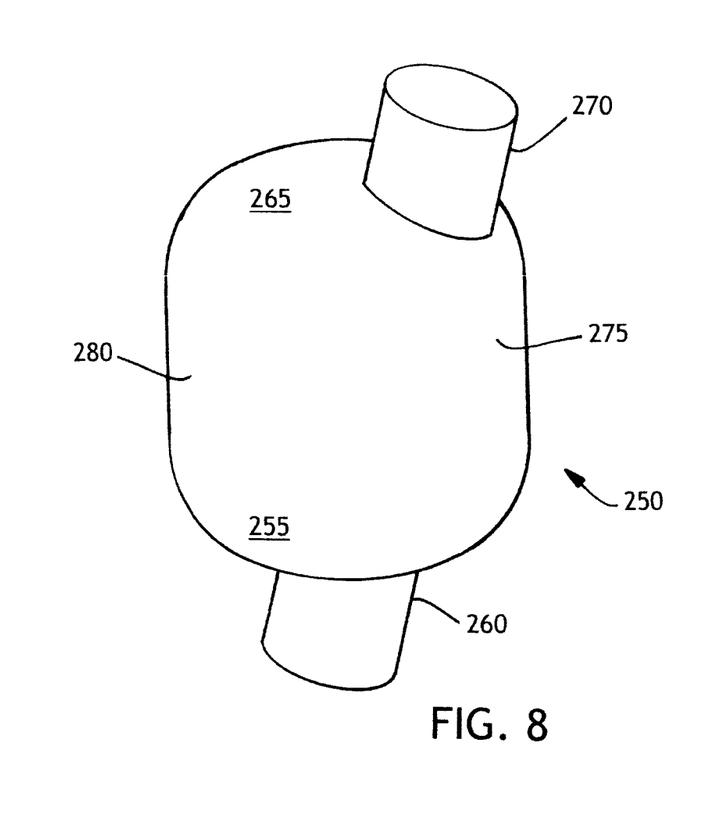
FIG. 8 is a perspective view of an exemplary inflatable balloon component.
Figure 9:
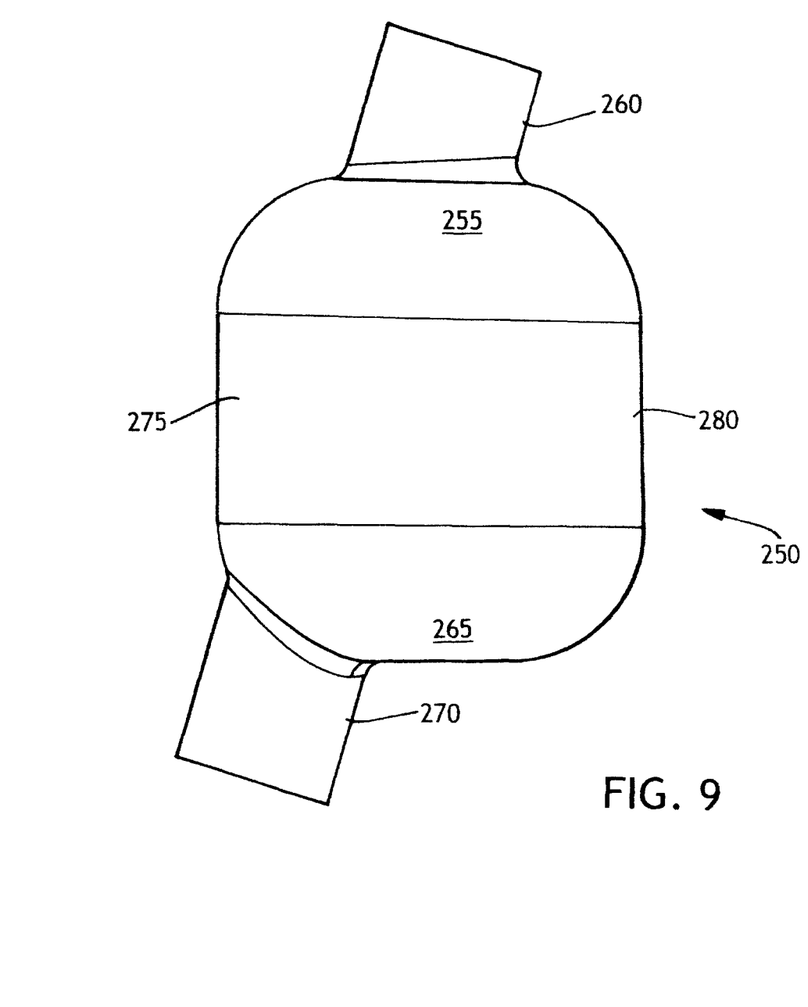
FIG. 9 which is a side view of an exemplary inflatable balloon component.

FIG. 8 is a perspective view of the resulting inflatable balloon component 250. FIG. 9 is a side view of the same balloon. This inflatable balloon component may include a distal end 255, a distal attachment zone 260, a proximal end 265, a proximal attachment zone 270, an upper region 275 and a lower region 280. According to an embodiment of the disclosure and as noted above, the upper region desirably has a thickness of from about 15 to about 30 micrometers and the lower region desirably has a thickness of from about 5 to about 15 micrometers. Extrapolating the locations of P, R and the proximal tube results in a location for their intersection at a point relatively far from proximal end 265 of the balloon 250. Nevertheless, this configuration allows for an opening between the proximal end of the balloon and the cranial edge of the stoma. As may also be clearly seen by reference to FIGS. 9 and 10, the distal end 260 of the tube exits the balloon substantially on center while the proximal end 270 of the tube exits the balloon in a position that is substantially off center to end of the balloon.

Figure 10:
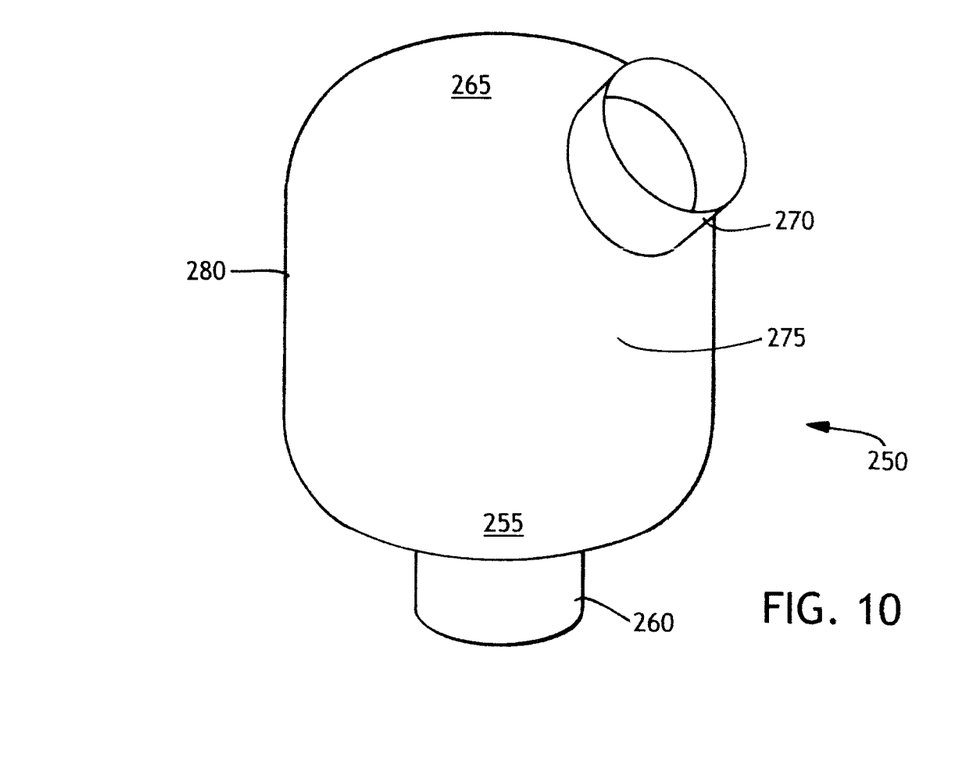
FIG. 10 is a perspective view of another embodiment of an exemplary inflatable balloon component.
Figure 11:
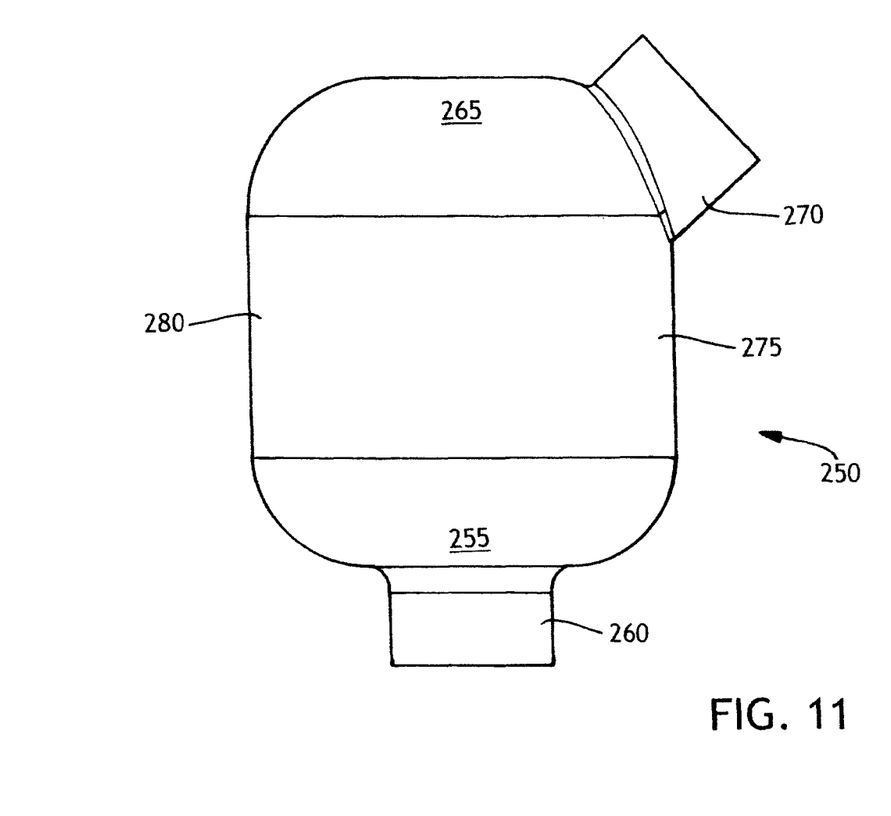
FIG. 11 which is a side view of another embodiment of an exemplary inflatable balloon component.

FIG. 10 is a perspective view of another embodiment of the resulting inflatable balloon component 250 and FIG. 11 is a side view of the same balloon. As can be seen in FIGS. 10 and 11, the inflatable balloon component may include a distal end 255, a distal attachment zone 260, a proximal end 265, a proximal attachment zone 270, an upper region 275 and a lower region 280. According to an embodiment of the instant disclosure, the upper region desirably has a thickness of from about 15 to about 30 micrometers and the lower region desirably has a thickness of from about 5 to about 15 micrometers. Extrapolating the locations of P, R and the proximal tube results in a location for their intersection at a point relative near to the proximal end 265 of the balloon 250. This configuration also clearly allows for a relatively large opening between the proximal end of the balloon and the cranial edge of the stoma. As may also be clearly seen by reference to FIGS. 11 and 12, the distal end 260 of the tube exits the balloon substantially on center while the proximal end 270 of the tube exits the balloon in a position that is substantially off center to the end of the balloon.

In reference to FIGS. 8 through 11 generally, the dimensions from the upper region 275 to the lower region 280 may range from about 50 millimeters to about 25 millimeters and may desirably be between about 35 millimeters to about 30 millimeters. The dimensions from the distal end 255 to the proximal end 265 may range from about 60 millimeters or more to about 25 millimeters and may desirably be between about 40 millimeters to about 30 millimeters. These are general dimensions and it is contemplated that the dimensions may be larger or smaller.

In the practice of the disclosed technology, the balloon component may be formed from thermoplastic polyurethane polymers, thermoplastic polyolefin elastomers, thermoplastic polyolefin block copolymers, SBS di-block elastomers, SEBS tri-block elastomers, polyvinyl chloride (PVC), polyethylene terephthalate (PET) and blends and mixtures thereof. More desirably, polyurethane may be used because it has been found to cause less irritation to tissues than other materials. Useful polyurethanes include those from the Dow Chemical Company (Dow Plastics) available under the tradename Pellethane®. Pellethane® thermoplastic polyurethane elastomer is available in a number of grades and hardnesses and the particular one selected for a specific use will depend on the properties desired in the final product. The hardness of a polymer, for example, is an attribute that may be varied to meet the requirements of various applications. One exemplary polyurethane is designated Pellethane® 2363-90A and has a durometer hardness of 90A (ASTM D-2240). This polyurethane has a softening temperature of 110° C. (ASTM D-790) and a melt index of 30 g/10 min. at 224° C., 2160 g (ASTM D-1238).

The device further includes means for inflating and deflating the balloon (not shown). These means for inflating and deflating the balloon may be conventional flexible conduits and fittings. In another aspect of the invention, the tracheostomy tube device may further include a flexible conduit (e.g. suction line or lumen) along the tube and the balloon such that secretions eventually accumulating cranially to the tracheal stoma can be removed. Suction may be applied to the proximal end of the conduit or lumen that terminates just above the balloon.

Figure 12:
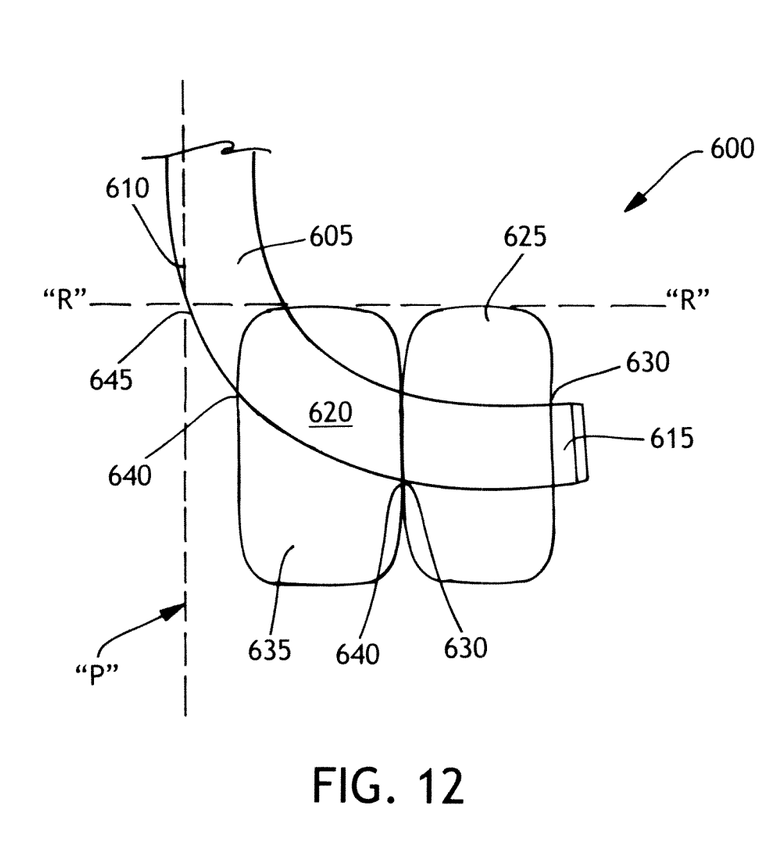
FIG. 12 is an illustration of an exemplary tracheostomy tube device having multiple inflatable balloons.

Yet another aspect of the invention encompasses a tracheostomy tube device having multiple inflatable balloons. As shown in FIG. 12, the tracheostomy tube device 600 includes a conventional hollow tube 605 having a proximal end portion 610, a distal end portion 615, and a bend region 620 intermediate of the end portions. The distal end portion of the tube is arranged for insertion through a patient's throat and tracheal stoma and into the tracheal lumen such that the distal end portion of the tube extends in a first direction within the tracheal lumen when the proximal end portion extends in a second direction through the tracheal stoma. The proximal end portion defines a proximal plane of the device The device further includes a first inflatable balloon 625 enveloping the distal end 615 of the tube, the first inflatable balloon 625 being substantially centered about and attached to the distal end of the tube at attachment zones 630.

The device also includes a second inflatable balloon 635 enveloping and attached to at least a portion of the bend region 620 of the tube and positioned substantially off-center about the bend region 620 below the proximal plane of the device "P". The second inflatable balloon 635 is attached to the tube at attachment zones 640.

Upon inflation, this configuration provides for expansion of the first inflatable balloon 625 around the distal end portion of the tube 615 and expansion of the second inflatable balloon 635 near the proximal end portion of the tube 610 below the proximal plane of the device "P" to seal the trachea below the tracheal stoma and avoid sealing the trachea above the tracheal stoma. Desirably, this configuration of the balloon to allow secretions to exit the stoma.

As noted above, while various curvatures of the bend region of conventional hollow tracheal tubes may result the proximal plane being located slightly more or slightly less forward, the proximal plane of the device "P" may be readily determined from a reference line "R" running parallel to the upper surface of the inflatable balloons 625 and 635 (while inflated). The proximal plane of the device "P" is the plane running perpendicular to the point 645 where the reference line "R" intersects with the most proximal or outermost portion of the tube 605. This is generally thought to correspond to a plane that runs along the portion of the tube as it passes the stoma just inside the tracheal lumen that is closest to the patient's head.

The device further includes means for inflating and deflating the balloon. The means for inflating and deflating the balloon may be a conventional flexible conduit in communication with each balloon. Alternatively, the means for inflating and deflating the balloon may be a conventional flexible conduit in communication with both balloons such that both balloons can be inflated and deflated simultaneously through a single conduit.

In an aspect of the invention, the second balloon may have walls having a non-uniform thickness. For example, a first portion of the second balloon may have walls having a thickness of about 20 to 30 micrometers and a second portion of the second balloon may have walls having a thickness of about 5 to about 15 micrometers. Desirably, the first portion of the second balloon is the portion of the balloon contacting the upper portion of a cross-sectional region of the tracheal lumen and the second portion of the second balloon is the portion of the balloon contacting the lower portion of the same cross-sectional region of the tracheal lumen.

At least one of the balloons may be formed of thermoplastic polyurethane polymers, thermoplastic polyolefin elastomers, thermoplastic polyolefin block copolymers, SBS di-block elastomers, SEBS tri-block elastomers and blends and mixtures thereof.

This application is one of a group of commonly assigned patent application which are being filed on the same day. The group includes application Ser. No. 12/206,517 in the name of Brian Cuevas and is entitled "Improved Balloon Cuff Tracheostomy Tube"; application Ser. No. 12/206,560 in the name of Brian Cuevas and is entitled "Improved Balloon Cuff Tracheostomy Tube with Greater Ease of Insertion"; application Ser. No. 12/206,480 in the name of Brian Cuevas and is entitled "A Tubular Workpiece for Producing an Improved Balloon Cuff Tracheostomy Tube"; application Ser. No. 12/206,583 in the name of Brian Cuevas and is entitled "A Method of Making an Improved Balloon Cuff Tracheostomy Tube".

Modifications and variations of the present invention will be obvious to those of skill in the art from the foregoing detailed description. Such modifications and variations are intended to come within the scope of the following claims.

We claim:

1. A tracheostomy tube device comprising:
   a hollow tube having a center, a proximal end portion, a distal end portion, and a bend region intermediate of the end portions, wherein the distal end portion is arranged for insertion through a patient's throat and tracheal stoma and into the tracheal lumen such that the distal end portion of the tube extends in a first direction within the tracheal lumen when the proximal end portion extends in a second direction through the tracheal stoma, the proximal end portion defining a proximal plane of the device;
   an inflatable balloon having a center and enveloping the tube, the balloon having a distal balloon portion centered about and attached to the distal end portion of the tube and a proximal balloon portion attached to the bend region of the tube and positioned such that the center of the tube is at least one tube radius away from the center of the balloon about the bend region below the proximal plane of the device, wherein the balloon expands upon inflation around the distal end portion of the tube and the proximal end portion of the tube below the proximal plane of the device to seal the trachea below the tracheal stoma without sealing the tracheal stoma;

means for inflating and deflating the balloon.

2. The tracheostomy tube device of claim 1, wherein the means for inflating and deflating the balloon comprises a flexible conduit in communication with the balloon.

3. A tracheostomy device for insertion into a trachea through a tracheal stoma, comprising a tube and balloon, each having a center, wherein said balloon upon inflation seals the trachea below the tracheal stoma without sealing the tracheal stoma and wherein said balloon is positioned such that the center of the tube is at least one tube radius away from the center of the balloon about a proximal bend region of said tube and positioned such that the center of the tube is at the center of the balloon at a distal end of said tube.

* * * * *